United States Patent [19]

Peeling et al.

[11] Patent Number: 4,585,112
[45] Date of Patent: Apr. 29, 1986

[54] AUTOMATED FEEDING DEVICE

[76] Inventors: George C. Peeling, R.D. #5, Muncy, Pa. 17756; Clyde R. Peeling, R.D. #1, Allenwood, Pa. 17810

[21] Appl. No.: 628,501

[22] Filed: Jul. 6, 1984

[51] Int. Cl.⁴ .............................................. G07F 1/00
[52] U.S. Cl. .................................. 194/293; 119/51.13; 194/334
[58] Field of Search ................. 119/51.13; 221/82, 83, 221/86; 194/93

[56]     References Cited
U.S. PATENT DOCUMENTS

| | | | |
|---|---|---|---|
| 912,455 | 2/1909 | Finney | 221/82 |
| 1,722,942 | 7/1929 | Peterson | 221/82 |
| 2,275,985 | 3/1942 | Prins | 194/63 |
| 2,687,825 | 8/1954 | Galin et al. | 221/82 |
| 2,935,225 | 3/1960 | Jordan | 221/150 |
| 3,029,978 | 4/1962 | Gummere | 221/22 |
| 3,050,029 | 8/1962 | Appleton | 119/51.13 |
| 3,658,036 | 4/1972 | Caracappa | 119/51.13 |
| 3,741,162 | 6/1973 | Lopez | 119/51.13 |
| 3,893,592 | 7/1975 | Friedman | 222/14 |
| 3,900,007 | 8/1975 | Smith | 119/51.13 |
| 4,059,072 | 11/1977 | Vassallo | 119/51.13 |

OTHER PUBLICATIONS

P. Foster-Turley and Markowitz, A Captive Behavioral Enrichment Study with Asian Small-Clawed River Otters, 1982, pp. 29-37.

C. Gans and H. Mix, A Sequential Insect Dispenser for Behavorial Experiments, Feb. 1974, pp. 88-89.

Primary Examiner—Hugh R. Chamblee
Attorney, Agent, or Firm—Prutzman, Kalb, Chilton & Alix

[57]     ABSTRACT

An automated feeding device for dispensing living insects to caged animals comprises a support frame detachably connected to an animal cage, a removable cassette assembly connected to the support frame and having a bottom plate with an annular portion having a smooth upper surface and a dispensing aperture therethrough, a top plate with an annular array of individual cells to hold live insects, each cell having a smooth interior surface devoid of insect grippable protrusions and an access opening for alignment with the dispensing aperture of the bottom plate with the top plate being rotatably mounted to the bottom plate for successive alignment of the access opening of the cells with the dispensing aperture and with the top plate in mating engagement with the bottom plate so that the smooth upper surface closes off the abutting access opening of the cells, the cassette assembly being removably mounted to the support frame to permit selective replacement of the cassette assembly, and an advancement mechanism for advancing the top plate to successively align the access opening of the next adjacent cell with the dispensing aperture.

15 Claims, 4 Drawing Figures

AUTOMATED FEEDING DEVICE

BACKGROUND AND SUMMARY OF THE INVENTION

This invention relates to automated feeding devices and more particularly to an automated feeding device for dispensing living insects to caged animals.

It is common for zoos, museums, and schools to maintain live animals for observation in cages simulating natural habitat. The experience of observing a live animal up close can be educational and entertaining. For example, reptiles and amphibians are generally caged in aquariums or terrariums which permit close observation of the animal. Unfortunately, reptiles and amphibians are seldom active unless they are pursuing prey and therefore such displays generally lack animation or movement. Accordingly, it would be desirable to naturally stimulate movement of such caged animals. The introduction of live prey into the cage will stimulate movement of the animal as it pursues the prey and will allow the observer to experience predator-prey relationships first hand.

Accordingly, it is an object of the present invention to provide an automated feeding device for dispensing living insects to caged animals.

Another object of the invention is to provide an automated feeding device for effectively dispensing live insects without harming the insect yet preventing the insect from clinging to the feeding device.

A further object of the invention is to provide an automated feeding device for dispensing live insects which holds a plurality of insects in a cassette assembly for individual dispensing and which allows quick and easy reloading of the cassette assembly.

A further object of the invention is to provide a coin-actuated automated feeding device for dispensing living insects to caged animals.

Yet another object of the invention is to provide an automated feeding device for dispensing living insects which is cost efficient to manufacture, easy to maintain and clean, and durable in use.

Accordingly, it has been found that the foregoing and related objects can be obtained in an automated feeding device comprising a support frame adapted for detachable connection to an animal cage with an access opening for supporting a removable cassette assembly for dispensing live insects into the cage. The removable cassette assembly includes a top plate and bottom plate. The bottom plate has an annular portion with a smooth upper surface and a dispensing aperture therethrough. The top plate has an annular array of individual cells for holding live insects with each cell having a smooth interior surface devoid of insect-grippable protrusions and an access opening adapted for alignment with the dispensing aperture of the bottom plate. The top plate is rotatably mounted to the bottom plate for successive alignment of the access openings of the cells with the dispensing aperture. The top plate is in mating engagement with the bottom plate so that the smooth upper surface of the bottom plate closes off the abutting access opening of the cells. The cassette assembly is removably mounted to the support frame to permit selective replacement of the cassette assembly. An advancement apparatus is operationally connected to the cassette assembly for selective advancement of the top plate to successively align the access opening of the next adjacent cell with the dispensing aperture. Each cell has a predetermined configuration so that the array of cells forms a pin wheel gear to operationally compliment the advancement apparatus for rotating the top plate relative to the bottom plate.

DESCRIPTION OF THE PREFERRED EMBODIMENT

Figure 1:
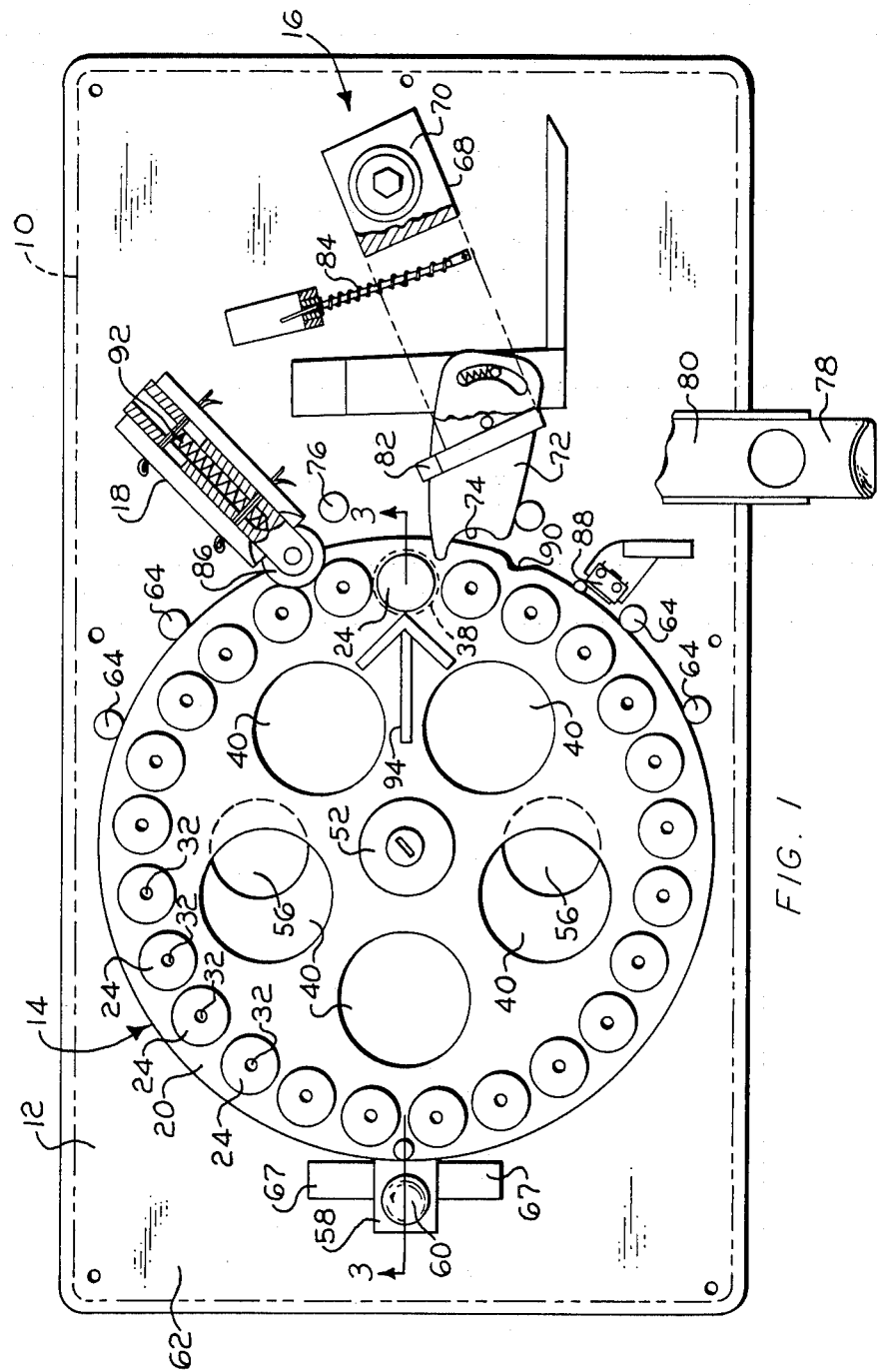
FIG. 1 is a plan view of the automated feeding device of the present invention mounted to a conventional aquarium (indicated in broken line) in an at-rest position.

Referring to FIG. 1, the automated feeding device of the present invention is shown mounted atop a conventional aquarium 10 indicated in broken line. The feeding device generally comprises a support frame 12, a removable cassette assembly generally designated by the numeral 14, a coin-actuated advance and alignment mechanism 16, and a detent 18.

The cassette assembly 14 has an upper plate 20 rotatably mounted to a lower plate 22. The upper plate 20 has a plurality of cylindrically shaped cells 24 orthogonally disposed about the outer periphery of the plate 20 to form an annular array. With the exception of the "dud" or alignment cell 24', the cells are identical so that only one need be described for purposes of explanation.

Each cell 24 forms an interior chamber 26 for holding a live insect with a smooth interior wall 28 devoid of protrusions for an insect to grip or cling to. The top 30 of each cell is integrally formed with the side wall 28 to also prevent the insect from clinging to the inside of the chamber 26. An air passageway 32 extends through the top 30 to provide air to the interior chamber 26. An access opening 34 to the chamber 26 opens outwardly from the bottom surface 36 of the upper plate 20 and is intended for alignment wit the dispensing aperture 38 of the lower plate 22. Preferably the access opening 34 is the same size or smaller than the dispensing aperture 38.

The access openings 34 of the cells 24 form an annular array in the bottom surface 36 of the upper plate 20. The "dud" cell 24' does not function to hold an insect but rather is utilized to align the upper plate 20 and the lower plate 22 when the cassette assembly 14 is fully loaded for mounting to the support frame 12. That is, the access opening of the cell 24' is blocked by a plug 44 which is in alignment with the dispensing aperture 38 when the cassette assembly is loaded. The upper plate 20 also has five equi-distant air vent apertures 40 and a central mounting aperture 42 for mounting the upper plate 20 to the lower plate 22.

Each cell 24 has a predetermined exterior configuration so that the array of cells form a gear wheel or sprocket for operative cooperation with the advance and alignment mechanism 16. In the illustrated embodiment, the cells 24 have a cylindrical configuration so that the array of cells form a pin wheel gear as can be seen in FIG. 1. As will be explained subsequently, the advance and alignment mechanism 16 engages an individual cylindrical cell 24 to advance the upper plate 20 relative to the lower plate 22. Preferably, the upper plate 20, including the array of cells 24, is an integral unitary structure, such as molded plastic material or the like with the interior walls of the chamber 26 forming a smooth continuous surface devoid of insect-grippable protrusions.

Figure 3:
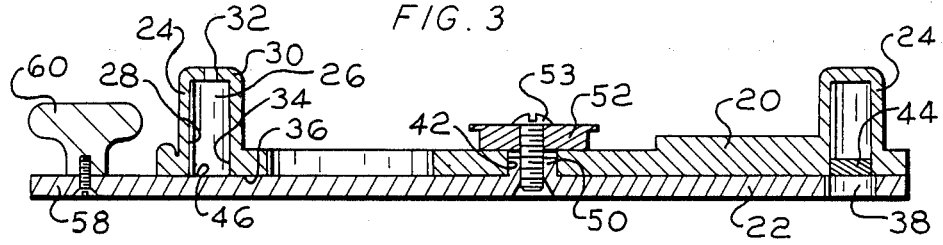
FIG. 3 is a sectional view seen on line 3—3 of FIG. 1.
Figure 4:
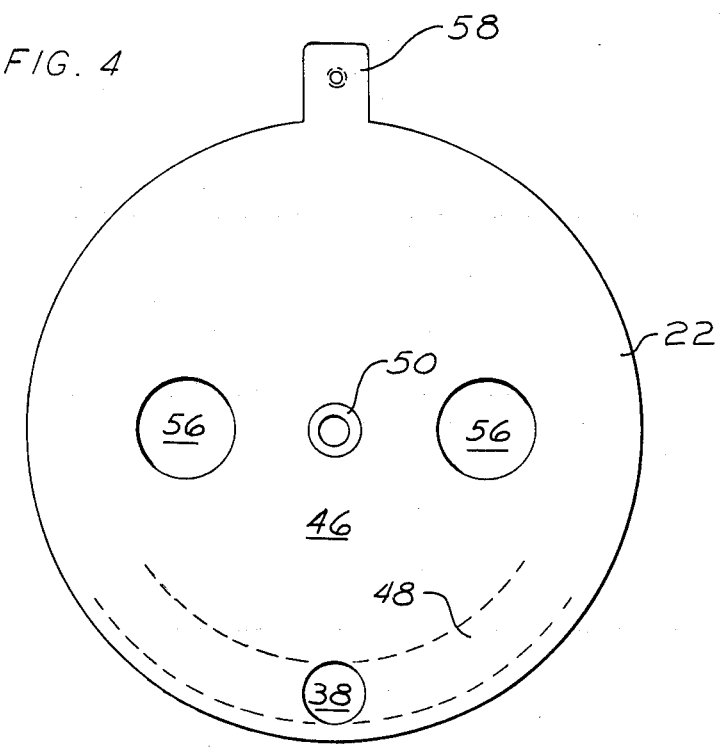
FIG. 4 is a plan view of the bottom plate of the cassette assembly.

Referring to FIGS. 3 and 4, the lower plate 22 has a top surface 46 wherein at least an annular portion 48 thereof (as indicated by dotted line in FIG. 3) is smooth for tight-fitting mating engagement with the bottom surface 36 of the upper plate 20 to close off the access openings 34 of the individual cells 24. The dispensing aperture 38 is disposed within the annular portion 48 for successive alignment with the individual access openings of the cells 24 as the upper plate is angularly rotated relative to the lower plate 22.

The lower plate 22 has a central shaft 50 for rotatably mounting the upper plate 20 to the lower plate 22. In assembly, the upper plate 20 is mounted tightly against the lower plate 22 with the shaft 50 extending through the central aperture 42 of the upper plate 20. A retaining ring 52 is utilized to detachably secure the upper plate 20 to the lower plate 22. The retaining ring 52 has a threaded bolt 53 to engage the correspondingly threaded bore 54 in the shaft 50. In this manner, the upper plate 20 is detachably connected for rotational movement relative to the lower plate 22 with the annular portion 48 of the lower plate 22 forming a closure for the access openings 34 of the cells 24. The close-fitting engagement between the upper plate 20 and the annular portion 48 prevents the insects from being caught and crushed between the upper and lower plates as the upper plate 20 is rotated relative to the lower plate 22.

The lower plate 22 also has a pair of air vent apertures 56 for permitting the passage of air to the aquarium 10 and a laterally extending leg 58 for aligning the lower plate onto the support frame 12. A lift knob 60 extends upwardly from the leg 58 to facilitate placement and removal of the cassette assembly 14 relative to the support frame 12.

The support frame 12 is adapted for mounting over the access opening of the conventional aquarium 10. The underside of the frame 12 (not shown) has a rectangular ridge to engage the interior side walls of the aquarium 10 to stabilize the frame 12 atop the aquarium. The upper side 62 of the support frame 12 is adapted to support the cassette assembly 14 so that the dispensing aperture 38 and the air vent apertures 56 of lower plate 22 are in alignment, respectively, with similar air vent apertures and a drophole of the support frame 12. To align or seat the cassette assembly 14 on the support frame 12, the upper side 62 has a plurality of upstanding alignment posts 64 disposed to engage the outer periphery of the cassette assembly 14 and a pair of upstanding studs 68 forming an alignment slot to receive the leg 58 of the lower plate 22. In assembly, the cassette assembly 14 simply overlies the support frame 12 and is maintained in proper alignment with the support frame 12 by the posts 64 and studs 68 without the need for fasteners or the like. In this manner, alignment and interchangeability of the cassette assembly 14 to the frame 12 is easily and conveniently attained.

Figure 2:
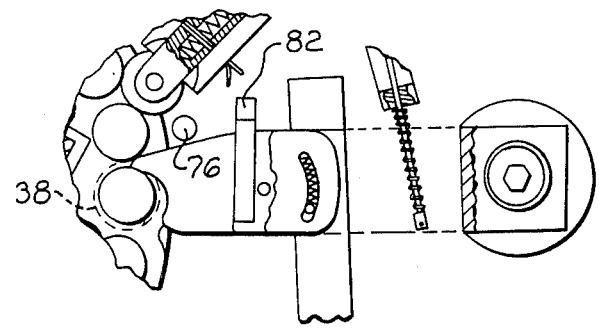
FIG. 2 is a partial view similar to FIG. 1 of the alignment and advance mechanism in an actuated position.

The advance and alignment mechanism 16 is mounted to the upper side 62 of the frame support 12 adjacent the cassette assembly 14 as shown in FIG. 1 and functions to advance the upper plate 20 relative to the lower plate 22 and align the next adjacent cell in registration with the dispensing aperture 38. The advance mechanism 16 comprises a segmented drive arm 68 pivotally mounted to the support frame 12 for movement between a first position as shown in FIG. 1 and a second position as shown in FIG. 2. The drive arm 68 has an inner segment 70 pivotally mounted at one end to the frame 12 and pivotally connected at the other end to an outer segment 72. The outer segment 72 has an asymmetrical concave recess 74 at its outer end to engage a cylindrical cell 24 and angularly rotate the upper plate 20 relative to the lower plate 22 as it pivots from the first position to the second position. An upstanding stud 76 acts as a stop to the pivotal movement of the outer segment 72 in the second position. The recess 74 is dimensioned and configured to position the engaged cell directly over the dispensing aperture 38 of the lower plate 22 when the drive arm 68 pivots to the second position.

A conventional coin actuator 78 is shown diagrammatically in FIG. 1 and functions to actuate movement of the pivot arm 68 to advance the top plate 20. The manual insertion of a coin into the actuator 78 extends an actuator arm 80 which in turns engages the upstanding post 82 of the inner segment 70 of the drive arm 68 to pivot the drive arm 68 from the first position to the second position. A compression spring 84 biases the drive arm 68 towards the first position to return the drive arm 68 to the first position after advancement of the upper plate 20.

Each cell 24 has a predetermined exterior configuration so that the array of cells forms a gear wheel complementary to the advance mechanism 16 for precise advancement and alignment of the upper plate 20 relative to the lower plate 22. In the illustrated embodiment, the exterior of each cell is cylindrical so that the array of cells forms a pin wheel gear and the drive arm has a complementary recess 74 to engage and angularly drive the pin wheel gear. Thus, the insect holding cells 24 perform a dual function and the necessity for a separate drive gear element on the upper plate 20 is eliminated. Other acceptable exterior configurations for the cells 24 may also be utilized to form an acceptable drive gear means cooperating with a complementary advance mechanism.

Referring to FIG. 1, the detent 18 functions to releasably maintain the respective cell 24 in alignment with the dispensing aperture 38 of the lower plate 22. The detent 18 is attached to the support frame 12 adjacent the cassette assembly 14 and has a roller 86 spring biased against the cylindrical cells 24. The detent 18 is positioned relative to the dispersing aperture 38 so as to maintain the respective cell 24 in alignment therewith. As the upper plate is advanced by the drive arm 68 so as to rotate the next adjacent cell into alignment with the dispensing aperture 38, the spring biased roller 86 yieldably retracts responsive to the angular movement of the upper plate 20. That is, as the upper plate 20 rotates counterclockwise as viewed in FIG. 1, the next adjacent downstream cell will cause the roller 86 to retract as it passes by. As the cell passes by, the roller 86 will then extend outward under the force of the biasing spring into engagement between the next adjacent pair of cells to maintain the upper plate in proper alignment. The extension of the roller 86 into engagement with the cells 24 causes a jarring force to the upper plate which functions to shake the insect loose.

In operation, the upper plate 20 is securely attached to the lower plate 22 by the retaining ring 52 to form the removable cassette assembly 14. To load the cassette assembly with live insects such as crickets, the assembly is inverted so that the lower plate 22 faces upwardly. The upper plate 20 is rotated to align the dispensing aperture 38 of the lower plate 22 into alignment with the access opening of one of the cells 24. As the live crickets may be very active and difficult to handle, a funnel may be utilized to guide the cricket into the dispensing aperture 38 without injuring it. Upon inserting the cricket into the cell, the upper plate is rotated to the next adjacent cell and the reloading process is repeated. When all the cells are loaded, the upper plate 20 is rotated so that the dud cell 24' as indicated by the indicia arrow 94 is positioned over the dispensing aperture 38. The fully loaded cassette assembly may be stored for future use or may be conveniently carried to the aquarium without loss or damage to the crickets.

A loaded cassette assembly is placed on the support frame 12 abutting the posts 64 with the leg 58 of the lower plate 22 inserted in the slot formed by the studs 67. In this position, the dispensing aperture 38 of the lower plate 22 is in alignment with the drophole of the support frame 12 to permit direct access to the aquarium 10.

Upon insertion of a coin into the coin actuator 78, the drive arm 68 is pivoted to its second position thereby engaging a cell 24 and angularly rotating the upper plate 20 so as to advance the cell adjacent the dud cell into alignment with the dispensing aperture 38. The cricket contained within this adjacent cell falls out of the cell through the dispensing aperture 38 and the drophole of the frame 12 into the aquarium 10.

The close-fitting engagement of the annular portion 48 against the access openings 34 of the cells 24 ensures that the remaining crickets will not be caught therebetween as the upper plate is advanced in succession. The compression spring 84 returns the drive arm 68 to the normal position. As the next adjacent cell is successively advanced into alignment with the aperture 38, another cricket is dispensed through the dispensing aperture and drophole into the aquarium 10. Since the interior chamber of the cell 24 is smooth without any protrusions for the cricket to grip, reliable dispensing is attained. Furthermore, accurate alignment of the access opening 34 of the cell with the dispensing aperture 38 assures that the cricket will not become caught or hung up on the lower plate 22.

During the time the cassette 14 is mounted to the support frame 12, the animal in the aquarium 10 receives air through the air vents 40, 56 of the cassette assembly 14. The number and spacing of the air vents 40 in the upper plate 20 ensures that the air vents 56 of the lower plate 22 are always open to the atmosphere as the upper plate 20 rotates relative thereto. The crickets contained within the cells 24 receive air through the air passageways 32 at the upper ends of the cells.

When the cassette assembly 14 is empty, an electrical switch 88 senses a notch 90 in the circumferential edge of the plate 20 and turns on an indicator light to indicate that the cassette is empty. The cassette is then removed and replaced with another preloaded cassette assembly. By preloading additional cassette assemblies in advance, there is no delay in restoring the device to an operational condition. This quick and easy replacement is advantageous to maximize usage. To clean the cassette assembly 14, the retaining ring 52 is removed and the upper plate 20 is separated from the lower plate 22 to permit convenient cleaning of the cells 24 and the upper surface 46 of the lower plate 22.

Accordingly, an automated feeding device for effectively dispensing live insects to caged animals is provided wherein the insects are held in a replaceable, reloadable cassette assembly and selectively dispensable therefrom without harm to the insects.

As will be apparent to persons skilled in the art, various modifications and adaptations of the structure above described will become readily apparent without departure from the spirit and scope of the invention, the scope of which is defined in the appended claims.

We claim:

1. An automated feeding device for dispensing living insects to caged animals comprising,
   a support frame means adapted for detachable connection to an animal cage with an access opening for supporting a removable cassette assembly for dispensing live insects into the cage,
   a removeable cassette assembly having,
      a bottom plate with an annular portion having a smooth upper surface and a dispensing aperture therethrough,
      a top plate with an annular array of individual cells for holding live insects, each cell being adapted to hold a live insect and having a smooth interior surface devoid of insect-grippable protrusions and an access opening adapted for alignment with the dispensing aperture of said bottom plate to dispense the insect contained within said cell through said dispensing aperture,
      said top plate being detachably connected and rotatably mounted to said bottom plate for successive aligment of the individual access openings of the cells with said dispensing aperture, said top plate being in mating engagement with said bottom plate so that said smooth upper surface of said bottom plate closes off the abutting access openings of said cells to maintain the insects within said cells and tightly engages said top plate to restrain an insect within a cell from being jammed between said top and bottom plate as said top plate is advanced relative to said bottom plate,
   said cassette assembly being removably mounted to said support frame means to permit selective replacement of said cassette assembly, said cassette assembly being mounted to said support frame means so that said dispensing aperture of said bottom plate is aligned with said access opening of the cage,
   means for aligning the access opening of an individual cell with said dispensing aperture of said bottom plate and for selectively advancing said top plate to successively align the access opening of the next adjacent cell with said dispensing aperture,
   each said cell having a predetermined exterior configuration so that said array of cells forms a gear wheel with said aligning and advancing means having means operationally complementing said gear wheel for rotating said top plate, and
   manually actuable means for actuating said aligning and advancing means.

2. The device of claim 1 wherein said top plate is detachably connected to said bottom plate by fastener means.

3. The device of claim 1 wherein said support frame means comprises a cover plate adapted for mounting to a conventional aquarium to cover the access opening of said aquarium, said cover plate having an access aperture in alignment with said dispensing aperture of said bottom plate when said bottom plate is mounted to said cover plate.

4. The device of claim 1 wherein said cells are integral to said top plate, said top plate having opposing top and bottom surfaces with said bottom surface defining the access openings of said cells and being in adjoining disposition to said bottom plate, each said cell being cylindrically shaped and extending outwardly from said top surface of said plate.

5. The device of claim 4 wherein said cylindrical cells are orthogonally disposed relative to said plate.

6. The device of claim 5 wherein said top plate is an integrally molded structure.

7. The device of claim 4 wherein each said cell has an air hole for providing air to an insect within said cell.

8. The device of claim 1 wherein each said cell has a cylindrical exterior configuration so that said array of cells forms a pin gear wheel.

9. The device of claim 8 wherein said aligning and advancing means comprises a spring biased detent means dimensioned and configured to engage said pin gear wheel to align the access opening of one of said cells with said dispensing aperture.

10. The device of claim 9 wherein said detent means comprises a detent roller spring biased into engagement with said cells forming said pin gear wheel, said detent roller being intermittently retracted by angular advancement of said top plate with the movement of said detent roller from an intermittently retracted position to an extended position jarring said top plate to shake loose an insect held within the respective cell aligned with said dispensing aperture.

11. The device of claim 1 wherein each said cell as a predetermined exterior configuration so that said array of cells forms a pin gear wheel and said aligning and advancing means comprises a drive arm movably mounted between first and second positions and having an outer end dimensioned and configured to engage and angularly drive said pin gear wheel to advance the cell adjacent said dispensing aperture into dispensing alignment with said dispensing aperture as said arm moves from said first position to said second position.

12. The device of claim 11 wherein each said cell has a cylindrical exterior configuration and said outer end of said drive arm has an asymmetric recess to engage a single cell and angularly drive said pin gear wheel as said arm moves from said first position to said second position.

13. The device of claim 1 wherein each said access opening of said cells is dimensionally no greater than said dispensing aperture.

14. The device of claim 13 wherein said access opening is dimensionally smaller than said dispensing aperture.

15. An automated feeding device for dispensing living insects to caged animals comprising,
 a support frame means adapted for detachable connection to an animal cage with an access opening for supporting a removable cassette assembly for dispensing live insects into the cage,
 a removeable cassette assembly having,
  a bottom plate with an annular portion having a smooth upper surface and a dispensing aperture therethrough,
  a top plate with an annular array of individual cells for holding live insects, each cell being adapted to hold a live insect and having a smooth interior surface devoid of insect-grippable protrusions and an access opening adapted for alignment with the dispensing aperture of said bottom plate to dispense the insect contained within said cell through said dispensing aperture,
  said top plate being detachably connected and rotatably mounted to said bottom plate for successive alignment of the individual access openings of the cells with said dispensing aperture, said top plate being in mating engagement with said bottom plate so that said smooth upper surface of said bottom plate closes off the abutting access openings of said cells to maintain the insects within said cells and tightly engages said top plate to restrain an insect within a cell from being jammed between said top and bottom plate as said top plate is advanced relative to said bottom plate,
 said cassette assembly being removably mounted to said support frame means to permit selective replacement of said cassette assembly, said cassette assembly being mounted to said support frame means so that said dispensing aperture of said bottom plate is aligned with said access opening of the cage,
 means for aligning the access opening of an individual cell with said dispensing aperture of said bottom plate and for selectively advancing said top plate to successively align the access opening of the next adjacent cell with said dispensing aperture,
 each said cell having a predetermined exterior configuration so that said array of cells forms a gear wheel with said aligning and advancing means having means operationally complementing said gear wheel for rotating said top plate, and
 coin-operated actuating means for actuating said aligning and advancing means.

* * * * *